United States Patent [19]

Rüger et al.

[11] Patent Number: 5,055,483
[45] Date of Patent: Oct. 8, 1991

[54] NOVEL AMINO ACID GLYCERIDES, LEARNING MEDICAMENTS CONTAINING THEM AND THEIR USE

[75] Inventors: Wolfgang Rüger, Kelkheim; Hansjörg Urbach, Kronberg; Reinhard Becker, Wiesbaden; Franz Hock, Dieburg, all of Fed. Rep. of Germany

[73] Assignee: Hoechst Aktiengesellschaft, Frankfurt am Main, Fed. Rep. of Germany

[21] Appl. No.: 299,186

[22] Filed: Jan. 19, 1989

[30] Foreign Application Priority Data

Jan. 21, 1988 [DE] Fed. Rep. of Germany ....... 3801587

[51] Int. Cl.$^5$ ................ C07D 209/02; C07D 207/12; A61K 31/40
[52] U.S. Cl. .................... 514/412; 514/414; 514/423; 548/452; 548/496; 548/530
[58] Field of Search ................ 548/496, 452, 530; 519/423, 412, 414

[56] References Cited

FOREIGN PATENT DOCUMENTS 0243645 3/1987 European Pat. Off. .
87/2230 10/1987 South Africa .

*Primary Examiner*—David B. Springer
*Attorney, Agent, or Firm*—Finnegan, Henderson, Farabow, Garrett, and Dunner

[57] ABSTRACT

The invention relates to amino acid esters of the formula

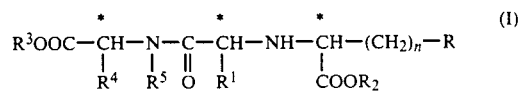

in which n=1 or 2, R, $R^1$, $R^2$ and $R^3$ denote hydrogen or a defined radical, $R^4$ together with $R^5$ and the atoms carrying them form a heterocyclic ring system, processes for their preparation, agents containing them and their use.

10 Claims, No Drawings

NOVEL AMINO ACID GLYCERIDES, LEARNING MEDICAMENTS CONTAINING THEM AND THEIR USE

The invention relates to amino acid esters of the formula I

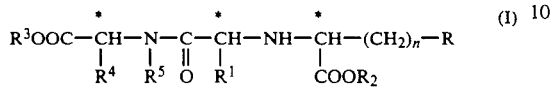

in which
n = 1 or 2,
R = hydrogen,
an optionally substituted aliphatic radical with 1–21 carbon atoms,
an optionally substituted alicyclic radical with 3–20 carbon atoms,
an optionally substituted aromatic radical with 6–12 carbon atoms,
an optionally substituted araliphatic radical with 7–32 carbon atoms,
an optionally substituted alicyclic-aliphatic radical with 7–14 carbon atoms,
an optionally substituted heteroaromatic or heteroaromatic-($C_1$–$C_8$)-aliphatic radical with 5–12 ring atoms or
a radical $OR^a$ or $SR^a$, in which
$R^a$ stands for an optionally substituted aliphatic radical with 1–4 carbon atoms, or an optionally substituted aromatic radical with 6–12 carbon atoms or an optionally substituted heteroaromatic radical with 5–12 ring atoms,
$R^1$ denotes hydrogen,
an optionally substituted aliphatic radical with 1–21 carbon atoms,
an optionally substituted alicyclic radical with 3–20 carbon atoms,
an optionally substituted alicyclic-aliphatic radical with 4–20 carbon atoms,
an optionally substituted alicyclic-aliphatic radical with 4–20 carbon atoms,
an optionally substituted aromatic radical with 6–12 carbon atoms,
an optionally substituted heteroaromatic or heteroaromatic-($C_1$–$C_8$)-aliphatic radical with 5–12 ring atoms or,
if not already included in the above definitions, the side chain, protected if necessary, of a naturally occurring α-amino acid,
$R^2$ and $R^3$ are identical or different and denote hydrogen, an optionally substituted aliphatic radical with 1–21 carbon atoms, an optionally substituted alicyclic radical with 3–20 carbon atoms,
an optionally substituted aromatic radical with 6–12 carbon atoms,
an optionally substituted araliphatic radical with 7–32 carbon atoms,
a radical of the formula

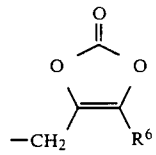

in which $R^6$ is hydrogen, an aliphatic radical with 1–6 carbon atoms or an optionally substituted aromatic radical with 6–12 carbon atoms,
a radical of the formula

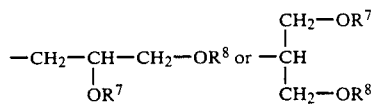

in which $R^7$ and $R^8$ are identical or different and independently of one another denote hydrogen, an optionally substituted unbranched or branched saturated or unsaturated alkyl radical with 1–23 carbon atoms or an optionally substituted unbranched or branched saturated or unsaturated acyl radical with 1–23 carbon atoms,
in which at least one of the radicals $R^2$ or $R^3$ denotes a radical of the formula

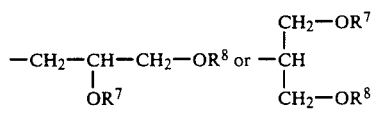

and
$R^4$ and $R^5$, together with the atoms carrying them, form a mono-, bi- or tricyclic heterocyclic ring system with 3 to 15 ring carbon atoms,
and physiologically tolerated salts thereof with acids and bases.

An optionally substituted unbranched or branched saturated or unsaturated acyl radical is preferably a radical of an aliphatic carboxylic acid, in particular saturated or unsaturated alkanoyl, such as, for example, formyl, acetyl, propionyl, butyryl, valeryl, isovaleryl, pivaloyl, lauroyl, myristoyl, palmitoyl, stearoyl, acryloyl, propioloyl, methacryloyl, crotonoyl, isocrotonoyl, oleoyl, elaidoyl, acetoacetyl, behenoyl, caprinoyl, caproyl, capryloyl, sorboyl, levulinoyl, lignoceroyl, enanthoyl, pelargonoyl, ricinoloyl or tigloyl. Medium- or longer-chain fatty acid esters such as occur, for example, in natural triglycerides are preferred.

An optionally substituted aliphatic radical is understood as an aliphatic acyclic radical, that is to say a radical with an open straight or branched carbon chain, such as, for example, alkyl, alkenyl, alkynyl and corresponding polyunsaturated radicals. It is unsubstituted or monosubstituted as described below, for example for carboxyl, carbamoyl, aminoalkyl, alkanoylaminoalkyl, alkoxycarbonylaminoalkyl, arylalkoxycarbonylaminoalkyl, arylalkylaminoalkyl, alkylaminoalkyl, dialkylaminoalkyl, alkylthioalkyl, arylthioalkyl, carboxyalkyl, carbamoylalkyl, alkoxycarbonylalkyl, alkanoyloxyalkyl, alkoxycarbonyloxyalkyl, aroyloxyalkyl or aryloxycarbonyloxyalkyl.

An optionally substituted alicyclic radical and the corresponding optionally substituted alicyclic-aliphatic radical bonded via an open carbon chain is a preferably mono-, di-, tri-, tetra- or pentacyclic isocyclic, non-aromatic radical with single or unsymmetrically distributed double bonds, which can also be branched (that is to say carry open-chain aliphatic side chains) and is linked via a ring carbon atom or a side chain carbon atom. It is preferably unsubstituted. Several rings as components of such a radical are fused, spiro-linked or isolated. Examples of such radicals are cycloalkyl, cycloalkenyl, cycloalkylalkyl, bicycloalkyl, tricycloalkyl and radicals derived from mono-, bi- or oligocyclic terpenes, such as menthyl, isomenthyl, bornyl, caranyl, epibornyl, epiisobornyl, isobornyl, norbornyl, neomenthyl, neoisomenthyl, pinanyl or thujanyl; they are preferably unsubstituted (aliphatic side chains are not substituents according to the present definition).

An optionally substituted aromatic radical is preferably aryl, such as phenyl, biphenylyl or naphthyl, which is optionally mono-, di- or trisubstituted as described below for aryl. Radicals derived from aryl, such as aralkyl, aryloxy, arylthio or aroyl, preferably benzoyl, can be substituted like aryl.

An optionally substituted heteroaromatic radical is preferably an aromatic mono- or bicyclic heterocyclic radical with 5 to 7 or 8 to 12, preferably up to 10, ring atoms, 1 or 2 ring atoms of which are sulfur or oxygen atoms and/or 1 to 4 ring atoms of which are nitrogen atoms, such as, for example, thienyl, benzo[b]thienyl, furyl, pyranyl, benzofuryl, pyrrolyl, imidazolyl, pyrazolyl, pyridyl, pyrimidinyl, pyridazinyl, indazolyl, isoindolyl, indolyl, purinyl, quinolizinyl, isoquinolinyl, phthalazinyl, naphthyridinyl, quinoxalinyl, quinazolyl, quinnolinyl, pteridinyl, oxazolyl, isoxazolyl, thiazolyl or isothiazolyl. These radicals can also be partly or completely hydrogenated. A heteroaromatic radical and the corresponding heteroaromatic-aliphatic radical can be substituted as defined below.

An optionally substituted araliphatic radical is understood, in particular, as phthalidyl or arylalkyl, diarylalkyl, indanyl or fluorenyl, in which aryl is as defined above and can be substituted in the manner described there.

$R^4$ and $R^5$ can form, with the atoms carrying these, a mono-, bi- or tricyclic heterocyclic ring system which has 3 to 15 ring carbon atoms and preferably contains up to 2 sulfur atoms and up to 2 nitrogen atoms, in particular up to 1 sulfur atom, in the ring.

Possible such ring systems are, in particular, those of the following group:

Tetrahydroisoquinoline (A); decahydroisoquinoline (B); octahydroindole (C); octahydrocyclopenta[b]pyrrole (D); 2-azaspiro[4.5]decane (E); 2-azaspiro[4.4]-nonane (F); spiro[(bicyclo[2.2.1]heptane)-2,3'-pyrrolidine] (G); spiro[(bicyclo[2.2.2]octane)-2,3'-pyrrolidine] (H); 2-azatricyclo[4.3.0.1$^{6,9}$]decane (I); decahydrocyclohepta[b]pyrrole (J); hexahydrocyclopropa[b]pyrrole (K); octahydroisoindole (L); octahydrocyclopenta[c]pyrrole (M); 2,3,3a,4,5,7a-hexahydroindole (N); 1,2,3,3a,4,6ahexahydrocyclopenta[b]pyrrole (O); pyrrolidine (P); indoline (Q) and thiazolidine (R), all of which can be optionally substituted.

Pyrrolidine (P) and thiazolidine (R) can be monosubstituted, for example by ($C_6$–$C_{12}$)-aryl (phenyl, 2-hydroxyphenyl and the like), ($C_6$–$C_{12}$)-arylmercapto (such as phenylmercapto) or ($C_3$–$C_7$)-cycloalkyl (such as cyclohexyl).

Tetrahydroisoquinoline (A) can carry, for example, up to 2 ($C_1$–$C_6$)-alkoxy radicals, preferably methoxy radicals, in the aryl part. Corresponding comments apply to the other ring systems. However, the unsubstituted systems are preferred.

The possible cyclic amino acid esters have the following structural formulae:

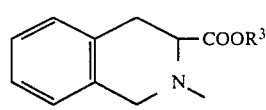

A

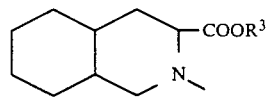

B

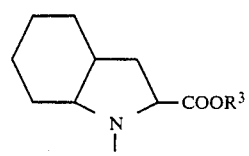

C

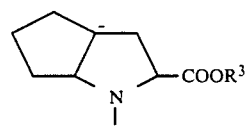

D

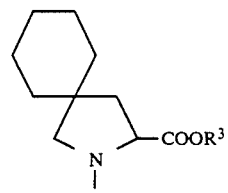

E

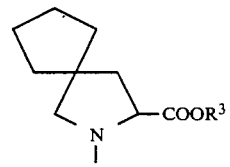

F

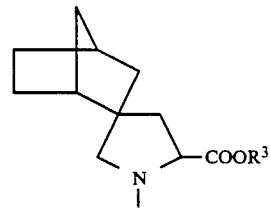

G

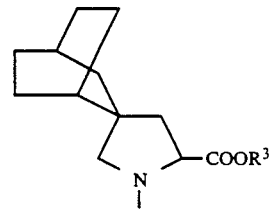

H

The ring systems A, C, D, H, O and P in which the carbon atom carrying the COOR³ group preferably has the S-configuration, are particularly preferred.

Examples of naturally occurring α-amino acids are Ala, Ser, Thr, Val, Leu, Ile, Asp, Asn, Glu, Gln, Arg, Lys, Hyl, Orn, Cit, Tyr, Phe, Trp and His.

If $R^1$ stands for a side chain of a protective naturally occurring α-amino acid, such as, for example, protected Ser, Thr, Asp, Asn, Glu, Gln, Arg, Lys, Hyl, Cys, Orn, Cit, Tyr, Trp or His, preferred protective groups are the groups customary in peptide chemistry (compare HoubenWeyl, Volume XV/1 and XV/2). In the case where $R^1$ denotes the protected lysine side chain, the known amino-protective groups are preferred, and in particular Z, Boc or ($C_1$–$C_6$)-alkanoyl. Possible O-protective groups for tyrosine are preferably ($C_1$–$C_6$)-alkyl, in particular methyl or ethyl.

The compounds of the formula I have asymmetric carbon atoms and can therefore occur as enantiomers and diastereomers. The invention relates both to the pure enantiomers and to the racemates.

In the case of compounds which have several chiral atoms, all the possible diastereomers, as racemates or enantiomers, or mixtures of various diastereomers, can be taken into consideration. The racemates can be resolved by customary methods, for example by salt formation with optically active acids, such as camphorsulfonic acid or di-benzoyltartaric acid, fractional crystallization and subsequent release of the bases from their salts, or by derivatization with suitable optically active reagents, separation of the diastereomeric derivatives by fractional crystallization or chromatography on silica gel or aluminum oxide and splitting back into the enantiomers. The diastereomers can be resolved by customary methods, such as fractional crystallization or chromatography on columns. Preferred compounds of the formula I are those in which a) n = 1 or 2;
b) R
  1. denotes hydrogen;
  2. denotes alkyl with 1–18 carbon atoms;
  3. denotes an aliphatic acyclic radical of the formula $C_aH_{(2a-b+1)}$, in which double bonds, if their number exceeds 1, are not cumulative, a stands for an integer from 2 to 18 and b stands for an integer from 2 to a;
  4. denotes a mono-, di-, tri-, tetra- or pentacyclic, non-aromatic hydrocarbon radical of the formula $C_cH_{(2c-d-1)}$, which is optionally branched, in which c stands for an integer from 3 to 20 and d stands for an even number from 0 to (C-2);
  5. denotes aryl which has 6–12 carbon atoms and can be mono-, di- or trisubstituted by ($C_1$–$C_8$)-alkyl, ($C_1$–$C_4$)alkoxy, hydroxyl, halogen, nitro, amino, aminomethyl, ($C_1$–$C_4$)alkylamino, di-($C_1$–$C_4$)-alkylamino, ($C_1$–$C_4$)alkanoylamino, methylenedioxy, carboxyl, cyano and/or sulfamoyl;

6. if n =2, denotes $(C_6-C_{12})$-aryl-$(C_1-C_8)$alkyl or di-$(C_6-C_{12})$-aryl-$(C_1-C_8)$-alkyl, each of which can be substituted in the aryl part as described under b) 5.; or denotes
7. alkoxy with 1-4 carbon atoms;
8. aryloxy which has 6-12 carbon atoms and can be substituted as described under b) 5.;
9. mono- or bicyclic heteroaryloxy or heteroaryl-$(C_1-C_8)$-alkyl which has 5-7 or 8-10 ring atoms, up to 9 ring atoms of which are carbon and 1 or 2 ring atoms of which are sulfur or oxygen and/or 1 to 4 ring atoms of which are nitrogen, and which can be substituted in the heteroaryl as described under b) 5.;
10. amino-$(C_1-C_8)$-alkyl;
11. $(C_1-C_4)$-alkanoylamino-$(C_1-C_8)$-alkyl;
12. $(C_7-C_{13})$-aroylamino-$(C_1-C_8)$-alkyl;
13. $(C_1-C_4)$-alkoxycarbonylamino-$(C_1-C_8)$-alkyl;
14. $(C_6-C_{12})$-aryl-$(C_1-C_4)$-alkoxycarbonylamino $(C_1-C_8)$-alkyl;
15. $(C_6-C_{12})$-aryl-$(C_1-C_4)$-alkylamino-$(C_1-C_8)$ alkyl;
16. $(C_1-C_4)$-alkylamino-$(C_1-C_8)$-alkyl;
17. di-$(C_1-C_4)$-alkylamino-$(C_1-C_8)$-alkyl;
18. guanidino-$(C_1-C_8)$-alkyl;
19. imidazolyl;
20. indolyl;
21. $(C_1-C_4)$-alkylthio;
22. if n =2, $(C_1-C_4)$-alkylthio-$(C_1-C_8)$-alkyl;
23. $(C_6-C_{12})$-arylthio-$(C_1-C_8)$-alkyl; which can be substituted in the aryl part as described under b) 5.;
24. $(C_6-C_{12})$-aryl-$(C_1-C_8)$-alkylthio, which can be substituted in the aryl part as described under b) 5.;
25. if n =2, carboxy-$(C_1-C_8)$-alkyl;
26. carboxyl;
27. carbamoyl;
28. if n =2, carbamoyl-$(C_1-C_8)$-alkyl;
29. $(C_1-C_4)$-alkoxycarbonyl-$(C_1-C_8)$-alkyl;
30. if n =2, $(C_6-C_{12})$-aryloxy-$(C_1-C_8)$-alkyl, which can be substituted in the aryl part as described under b) 5.; or
31. $(C_6-C_{12})$-aryl-$(C_1-C_8)$-alkoxy, which can be substituted in the aryl part as described under b) 5.;

c) $R^1$
1. denotes hydrogen;
2. denotes alkyl with 1-18 carbon atoms;
3. denotes an aliphatic acyclic radical of the formula $C_aH_{(2a-b+1)}$, wherein double bonds, if their number exceeds 1, are not cumulative, a stands for an integer from 2 to 18 and b stands for an even number from 2 to a;
4. denotes a mono-, di-, tri-, tetra- or pentacyclic, non-aromatic hydrocarbon radical of the formula $C_cH_{(2c-d-1)}$, which is optionally branched and in which c stands for an integer from 3 to 20 and d stands for an even number from 0 to (c-2); or denotes
5. aryl with 6-12 carbon atoms, which can be substituted as described under b) 5.;
6. $(C_6-C_{12})$-aryl-$(C_1-C_8)$-alkyl or $(C_7-C_{13})$-aroyl-$(C_1-C_8)$-alkyl, both of which can be substituted in the aryl part as described under b) 5.;
7. mono- or bicyclic optionally partly hydrogenated heteroary or heteroaryl-$(C_1-C_8)$-alkyl which has 5-7 or 8-10 ring atoms, up to 9 ring atoms of which are carbon and 1 or 2 ring atoms of which are sulfur or oxygen atoms and/or 1 to 4 ring atoms of which are nitrogen atoms, and which can be substituted in the heteroaryl as described for aryl under b) 5.; or
8. if not yet included in c) 1.-7., the side chain, protected if appropriate, of a naturally occurring α-amino acid of the formula $R^1$—CH(NH$_2$)—COOH;

d) $R^2$ and $R^3$ are identical or different and
1. denote hydrogen;
2. denote alkyl with 1-18 carbon atoms;
3. denote an aliphatic acyclic radical of the formula $C_aH_{(2a-b+1)}$, in which double bonds, if their number exceeds 1, are not cumulative, a stands for an integer from 2 to 18 and b stands for an even number from 2 to a;
4. denote a mono-, di-, tri-, tetra- or pentacyclic, non-aromatic hydrocarbon radical of the formula $C_cH_{(2c-d-1)}$, which is optionally branched and in which c stands for an integer from 3 to 20 and d stands for an even number from 0 to (c-2); or denote
5. di-$(C_1-C_4)$-alkylamino-$(C_1-C_8)$-alkyl;
6. $(C_1-C_5)$-alkanoyloxy-$(C_1-C_8)$-alkyl;
7. $(C_1-C_6)$-alkoxycarbonyloxy-$(C_1-C_8)$-alkyl;
8. $(C_7-C_{13})$-aroyloxy-$(C_1-C_8)$-alkyl;
9. $(C_6-C_{12})$-aryloxycarbonyloxy-$(C_1-C_8)$-alkyl;
10. aryl with 6-12 carbon atoms;
11. $(C_7-C_{20})$-aralkyl;
12. phthalidyl;
13. a radical of the formula

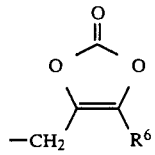

in which $R^6$ is hydrogen, $(C_1-C_6)$-alkyl or aryl with 6-12 carbon atoms, or
14. a radical of the formula

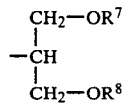

in which $R^7$ and $R^8$ are identical or different and independently of one another denote hydrogen, an optionally substituted unbranched or branched saturated or unsaturated alkyl radical with 1-23 carbon atoms or an optionally substituted unbranched or branched saturated or unsaturated acyl radical with 1-23 carbon atoms,
it being possible for the radicals mentioned under d) 8., 9., 10., 11. and 12. to be substituted in the aryl part as described under b) 5.; and
in which at least one of the radicals $R^2$ or $R^3$ denotes a radical of the formula

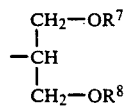

and
e) $R^4$ and $R^5$, together with the atoms carrying them, form a mono-, bi- or tricyclic heterocyclic ring system with 3 to 15 ring carbon atoms;

and physiologically tolerated salts thereof with acids and bases.

Particularly preferred compounds of the formula I are those in which n = 1 or 2,
R = hydrogen,
  alkyl with 1-8 carbon atoms,
  alkenyl with 2-6 carbon atoms,
  cycloalkyl with 3-9 carbon atoms,
  aryl which has 6-12 carbon atoms,
    and can be mono-, di- or trisubstituted by $(C_1-C_4)$-alkyl, $(C_1-C_4)$-alkoxy, hydroxyl, halogen, nitro, amino, aminomethyl $(C_1-C_4)$-alkylamino, di-$(C_1-C_4)$-alkylamino, $(C_1-C_4)$-alkanoylamino, methylenedioxy, carboxyl, cyano and/or sulfamoyl,
  alkoxy with 1-4 carbon atoms,
  aryloxy which has 6-12 carbon atoms
    and can be substituted as described above for aryl,
  mono- or bicyclic heteroaryloxy which has 5-7 or 8-10 ring atoms, 1 or 2 ring atoms of which are sulfur or oxygen atoms and/or 1 to 4 ring atoms of which are nitrogen,
    and which can be substituted as described above for aryl,
  amino-$(C_1-C_4)$-alkyl,
  $(C_1-C_4)$-alkanoylamino-$(C_1-C_4)$-alkyl,
  $(C_7-C_{13})$-aroylamino-$(C_1-C_4)$-alkyl,
  $(C_1-C_4)$-alkoxycarbonylamino-$(C_1-C_4)$-alkyl,
  $(C_6-C_{12})$-aryl-$(C_1-C_4)$-alkoxycarbonylamino-$(C_1-C_4)$alkyl,
  $(C_6-C_{12})$-aryl-$(C_1-C_4)$-alkylamino-$(C_1-C_4)$-alkyl,
  $(C_1-C_4)$-alkylamino-$(C_1-C_4)$-alkyl,
  di-$(C_1-C_4$-alkylamino-$(C_1-C_4)$-alkyl,
  guanidino-$(C_1-C_4)$-alkyl,
  imidazolyl, indolyl,
  $(C_1-C_4)$-alkylthio,
  $(C_1-C_4)$-alkylthio-$(C_1-C_4)$-alkyl,
  $(C_6-C_{12})$-arylthio-$(C_1-C_4)$-alkyl,
    which can be substituted in the aryl part as described above for aryl,
  $(C_6-C_{12})$-aryl-$(C_1-C_4)$-alkylthio,
    which can be substituted in the aryl part as described above for aryl,
  carboxy-$(C_1-C_4)$-alkyl,
  carboxyl, carbamoyl,
  carbamoyl-$(C_1-C_4)$-alkyl,
  $(C_1-C_4)$-alkoxycarbonyl-$(C_1-C_4)$-alkyl,
  $(C_6-C_{12})$-aryloxy-$(C_1-C_4)$-alkyl,
    which can be substituted in the aryl part as described above for aryl, or
  $(C_6-C_{12})$-aryl-$(C_1-C_4)$-alkoxy,
    which can be substituted in the aryl part as described above for aryl,
$R^1$ denotes hydrogen,
  alkyl with 1-6 carbon atoms,
  alkenyl with 2-6 carbon atoms,
  alkynyl with 2-6 carbon atoms,
  cycloalkyl with 3-9 carbon atoms,
  cycloalkenyl with 5-9 carbon atoms,
  $(C_3-C_9)$-cycloalkyl-$(C_1-C_4)$-alkyl,
  $(C_5-C_9)$-cycloalkenyl-$C_1-C_4)$-alkyl,
  optionally partly hydrogenated aryl which has 6-12 carbon atoms
    and can be substituted as described above for R,
  $(C_6-C_{12})$-aryl-$(C_1-C_4)$-alkyl or $(C_7-C_{13})$-aroyl$(C_{(C1}$ or $C_2)$-alkyl
    both of which can be substituted like the above aryl,
  mono- or bicyclic, optionally partly hydrogenated heteroaryl which has 5-7 or 8-10 ring atoms, 1 or 2 ring atoms of which are sulfur or oxygen atoms and/or 1 to 4 ring atoms of which are nitrogen atoms,
    and which can be substituted like the above aryl, or
  the side chain, protected if appropriate, of a naturally occurring α-amino acid $R^1$—CH(NH$_2$)—COOH,
and $R^3$ are identical or different and denote hydrogen,
  alkyl with 1-6 carbon atoms,
  alkenyl with 2-6 carbon atoms,
  di-$(C_1-C_4)$-alkylamino-$(C_1-C_4)$-alkyl,
  $(C_1-C_5)$-alkanoyloxy-$(C_1-C_4)$-alkyl,
  $(C_1-C_6)$-alkoxycarbonyloxy-$(C_1-C_4)$-alkyl,
  $(C_7-C_{13})$-aroyloxy-$(C_1-C_4)$-alkyl,
  $(C_6-C_{12})$-aryloxycarbonyloxy-$(C_1-C_4)$-alkyl,
  aryl with 6-12 carbon atoms,
  $(C_6-C_{12})$-aryl-$(C_1-C_4)$-alkyl,
  $(C_3-C_9)$-cycloalkyl,
  $(C_3-C_9)$-cycloalkyl-$(C_1-C_4)$-alkyl,
  phthalidyl,
  a radical of the formula

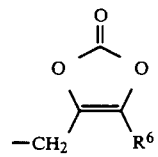

in which $R^6$ is hydrogen, $(C_1-C_6)$-alkyl or aryl with 6-12 carbon atoms,
or a radical of the formula

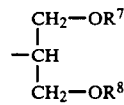

in which $R^7$ and $R^8$ are identical or different and independently of one another denote hydrogen or an optionally substituted unbranched or branched saturated or unsaturated acyl radical with 1-23 carbon atoms,
and in which at least one of the radicals $R^2$ or $R^3$ denotes a radical of the formula

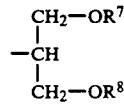

and
$R^4$ and $R^5$ have the abovementioned meaning, and physiologically tolerated salts thereof with acids and bases.

Especially preferred compounds of the formula I are those in which n = 1 or 2,

R denotes $(C_1-C_6)$-alkyl, $(C_2-C_6)$-alkenyl, $(C_3-C_9)$-cycloalkyl, amino-$(C_1-C_4)$-alkyl, $(C_2-C_5)$-acylamino$(C_1-C_4)$-alkyl, $(C_7-C_{13})$-aroylamino-$(C_1-C_4)$-alkyl, $(C_1-C_4)$-alkoxycarbonylamino-$(C_1-C_4)$-alkyl, $(C_6-C_{12})$-aryl-$(C_1-C_4)$-alkoxycarbonylamino-$(C_1-C_4)$-alkyl, $(C_6-C_{12})$-aryl, which can be mono-, di- or tri-substituted by $(C_1-C_4)$-alkyl, $(C_1-C_4)$-alkoxy, hydroxyl, halogen, nitro, amino, $(C_1-C_4)$-alkylamino, di-$(C_1-C_4)$-alkylamino and/or methylenedioxy, or 3-indolyl, in particular methyl, ethyl, cyclohexyl, tert.-butoxycarbonylamino-$(C_1-C_4)$-alkyl, benzyloxycarbonylamino-$(C_1-C_4)$-alkyl or phenyl, which can be mono- or disubstituted, or in the case of methoxy trisubstituted, by phenyl, $(C_1-C_2)$-alkyl, $(C_1$ or $C_2)$-alkoxyl, hydroxyl, fluorine, chlorine, bromine, amino, $(C_1-C_4)$-alkylamino, di-$(C_1-C_4)$-alkylamino, nitro and/or methylenedioxy, $R^1$ denotes hydrogen or $(C_1-C_6)$-alkyl, which can optionally be substituted by amino, $(C_1-C_6)$-acylamino or benzoylamino, $(C_2-C_6)$-alkenyl, $(C_3-C_9)$-cycloalkyl, $(C_5-C_9)$-cycloalkenyl, $(C_3-C_7)$-cycloalkyl-$(C_1-C_4)$-alkyl, $(C_6-C_{12})$-aryl or partly hydrogenated aryl, each of which can be substituted by $(C_1-C_4)$-alkyl, $(C_1$ or $C_2)$-alkoxy or halogen, $(C_6-C_{12})$-aryl-$(C_1-C_4)$-alkyl or $(C_7-C_{13})$-aroyl-$(C_1-C_2)$-alkyl, both of which can be substituted in the aryl radical as defined above, a mono- or bicyclic heterocyclic radical which has 5 to 7 or 8 to 10 ring atoms, 1 or 2 ring atoms of which are sulfur or oxygen atoms and/or 1 to 4 ring atoms of which are nitrogen, atoms, or a side chain of a naturally occurring α-amino acid, which is protected if appropriate, but in particular hydrogen, $(C_1-C_3)$-alkyl, $(C_2$ or $C_3)$-alkenyl, the side chain, protected if appropriate, of Lysine, phenylalanine or tyrosine, benzyl, 4-methoxybenzyl, 4-ethoxybenzyl, phenethyl, 4-aminobutyl or benzoylmethyl, $R^2$ and $R^3$ are identical or different radicals and denote hydrogen, $(C_1-C_6)$-alkyl, $(C_2-C_6)$-alkenyl, $(C_6-C_{12})$-aryl-$(C_1-C_4)$-alkyl, $(C_1-C_5)$-alkanoyloxy-$(C_1-C_4)$-alkyl, $(C_1-C_6)$-alkoxycarbonyloxy-$(C_1-C_4)$-alkyl, $(C_7-C_{13})$-aroyloxy-$(C_1-C_4)$-alkyl, $(C_6-C_{12})$-aryloxycarbonyloxy-$(C_1-C_4)$-alkyl, phthalidyl, a radical of the formula

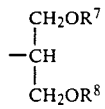

in which $R^6$ is hydrogen, $(C_1-C_6)$-alkyl or aryl with 6-12 carbon atoms, or a radical of the formula

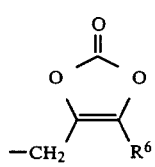

in which $R^7$ and $R^8$ denote hydrogen or a saturated or unsaturated acyl radical with 8-23 carbon atoms, and in which at least one of the radicals $R^2$ or $R^3$ denotes a radical of the formula

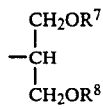

and $R^4$ and $R^5$ have the abovementioned meaning, and physiologically tolerated salts thereof with acids and bases.

Examples of especially preferred compounds are:

1,3-dihydroxy-2-propyl 2-[N-(1S-ethoxycarbonyl-3-phenyl-propyl)-S-alanyl]-1,2,3,4-tetrahydroisoquinoline-3S-carboxylate;

1,3-di(hexadecanoyloxy)-2-propyl 2-[N-(1S-ethoxycarbonyl-3-phenylpropyl)-S-alanyl]-1,2,3,4-tetrahydroisoquinoline-3S-carboxylate;

1,3-di-(9Z,12Z-octadecadienoyl)-2-propyl 2-[N-(1S-ethoxycarbonyl-3-phenylpropyl)-S-alanyl]-1,2,3,4-tetrahydroisoquinoline-3S-carboxylate;

1,3-di-(tetradecanoyloxy)-2-propyl 2-[N-(1S-carboxy-3-phenylpropyl)-S-alanyl]-1,2,3,4-tetrahydroisoquinoline-3S-carboxylate;

2-[N-[1S-[1,3-di-(octadecanoyloxy)-2-propyloxycarbonyl-3-phenylpropyl)-S-alanyl]-1,2,3,4-tetrahydroisoquinoline-3S-carboxylic acid;

n-octyl 2-[N-[1S-[1,3-di-(9Z,12Z,15Z-octadecatrienoyloxy)2-propyloxycarbonyl]-3-phenylpropyl]-S-alanyl]-1,2,3,4-tetrahydroisoquinoline-3S-carboxylate;

1,3-dihydroxy-2-propyl 2-[N-[1S-(1,3-dihydroxy-2-propyloxycarbonyl)-3-phenylpropyl]-S-alanyl]-1,2,3,4-tetrahydroisoquinoline-3S-carboxylate;

1,3-di-(octadecanoyloxy)-2-propyl 1-[N-(1S-ethoxycarbonyl-3-phenylpropyl)-S-alanyl]-(2S,3aR,7aS)-octahydro[1H]indole-2-carboxylate;

1,3-di-(5Z,8Z,11Z,14Z-eicosatetraenoyloxy)-2-propyl 1-[N-(1S-octyloxycarbonyl-3-phenylpropyl)-S-alanyl]-(2S,3aR,aS)-octahydro[1H]indole-2-carboxylate;

1,3-di-(hexadecanoyloxy)-2-propyl 1-[N-(1S-menthyloxycarbonyl-3-phenylpropyl)-S-alanyl]-(2S,3aR,7aS)-octahydro[1H]indole-2-carboxylate;

1,3-di-(tetradecanoyloxy)-2-propyl 1-[N-(1S-[1,3-di(tetradecanoyloxy)-2-propyloxycarbonyl]-3-phenylpropyl)S-alanyl]-(2S,3aR,7aS)-octahydro[1H]indole-2-carboxylate; (5-methyl-1,3-dioxolen-2-on-4-yl)methyl 1-[N-[1S-[1,3-di(9Z,12Z-octadecadienoyloxy)-2-propyloxycarbonyl]-3-phenylpropyl]-S-alanyl]-(2S,3aR,7aS)-octahydro[1H]indole-2-carboxylate;

5-nonyl 1-[N-[1S-(1,3-dihydroxy-2-propyloxycarbonyl)-3-phenylpropyl]-S-alanyl]-(2S,3aR,7aS)-octahydro[1H]indole-2-carboxylate;

1,3-di(hexadecanoyloxy)-2-propyl 1-[N-(1S-carboxy-3-phenylpropyl)-S-alanyl]-(2S,3aS,7aS)-octahydro[1H]indole-2-carboxylate;

1,3-di-(9Z,12Z,14Z-octadecatrienoyloxy)-2-propyl 1-[N-(1S-ethoxycarbonyl-3-phenylpropyl)-S-alanyl]-(2S,3aS,7aS)octahydro[1H]indole-2-carboxylate;

1,3-dihydroxy-2-propyl 1-[N-(1S-ethoxycarbonyl-3-phenylpropyl)-S-alanyl]-(2S,3aS,7aS)-octahydro[1H]indole-2-carboxylate;

1,3-di(hexadecanoyloxy)-2-propyl 1-[N-[1S-[1,3-di(hexadecanoyloxy)-2-propyloxycarbonyl]-3-phenylpropyl]-S-alanyl]-(2S,3aS,7aS)-octahydro[1H]indole-2-carboxylate; 1-[N-[1S-[1,3-di(octadecanoyloxy)-2-propyloxycarbonyl]-3-phenylpropyl]-S-alanyl]-(2S,3aS,7aS)-octahydro[1H]indole-2-carboxylic acid;

benzhydryl 1-[N-[1S-[1,3-di(9Z-octadecanoyloxy)-2-propyloxycarbonyl]-3-phenylpropyl]-S-alanyl]-(2S,3aS,7aS)octahydro[1H]indole-2-carboxylate;

1,3-dihydroxy-2-propyl 2-[N-(1S-ethoxycarbonyl-3-phenylpropyl)-S-alanyl]-(1S,3S,5S-2-azabicyclo[3.3.0]octane-3-carboxylate;

1,3-dipivaloyloxy-2-propyl 2-[N-(1S-ethoxycarbonyl-3-phenylpropyl)-S-alanyl]-(1S,3S,5S)-2-azabicyclo[3.3.0]octane-3-carboxylate;

1,3-di(decanoyloxy)-2-propyl 2[N-(1S-ethoxycarbonyl-3-phenylpropyl)-S-alanyl]-(1S,3S,5S)-2-azabicyclo[3.3.0]octane-3-carboxylate;

1,3-di(hexadecanoxyloxy)-2-propyl 2-[N-(1S-ethoxycarbonyl-3-phenylpropyl)-S-alanyl]-(1S,3S,5S)-2-azabicyclo3.3.0]octane-3-carboxylate;

1,3-di(octadecanoyloxy)-2-propyl 2-[N-(1S-ethoxycarbonyl-3-phenylpropyl)-S-alanyl]-(1S,3S,5S)-2-azabicyclo[3.3.0]octane-3-carboxylate;

1,3-di(5Z,8Z,11Z,14Z-eicosatetraenoyloxy)-2-propyl 2-[N-(1S-carboxy-3-phenylpropyl)-S-alanyl]-(1S,3S,5S)-2-azabicyclo[3.3.0]octane-3-carboxylate;

octyl 2-[N-[1S-[1,3-di(hexadecanoyloxy)-2-propyloxycarbonyl]-3-phenylpropyl]-S-alanyl]-(1S,3S,5S)-2-azabicyclo3.3.0]octane-3-carboxylate;

2-[N-[1S-[1,3-di(octadecanoyloxy)-2-propyloxycarbonyl]-3-phenylpropyl]-S-alanyl]-(1S,3S,5S)-2-azabicyclo[3.3.0]-octane-3-carboxylic acid;

1,3-dihydroxy2-propyl 2-[N-[1S-(1,3-dihydroxy-2-propyloxycarbonyl]-3-phenylpropyl]-S-alanyl]-(1S,3S,5S)-2-azabicyclo[3.3.0]octane-3-carboxylate;

decyl 2-[N-[1S-[1,3-di(9Z,12Z-octadecadienoyloxy)-2-propyloxycarbonyl]-3-phenylpropyl]-S-alanyl]-(1S,3S,5S)2-azabicyclo[3.3.0]octane-3-carboxylate;

1,3-dihexadecanoyloxy-2-propyl 1-[N-(1S-ethoxycarbonyl-3-phenylpropyl]-S-alanyl]-3'S-spiro[(bicyclo[2.2.2]octane)2,3'-pyrrolidine]-5'S-yl-carboxylate;

1-octadecanoyloxy-3-octadecanoyloxy-2-propyl 1-[N-(1S-octyloxycarbonyl-3-phenylpropyl]-S-alanyl]-3'S-spiro[(bicyclo[2.2.2]octane)-2,3'-pyrrolidine]-5'S-yl-carboxylate;

1,3-di(9Z,12Z,15Z-octadecatrienoyloxy)-2-propyl 1-[N-(1S-carboxy-3-phenylpropyl)-S-alanyl]-3'S-spiro[2.2.2]octane)-2,3'-pyrrolidine]-5'S-yl-carboxylate;

1,3-dihydroxy-2-propyl 1-[N-(1S-menthyloxycarbonyl-3-phenylpropyl]-S-alanyl]-3'S-spiro[(bicyclo[2.2.2]octane)-2,3'-pyrrolidine]-5'S-yl-carboxylate;

1,3-di(tetradecanoyloxy)-2-propyl 1-[N-[1S-[1,3-di(tetradecanoyloxy)-2-propyloxycarbonyl]-3-phenylpropyl]-S-alanyl]-3'S-spiro[(bicyclo[2.2.2]octane)-2,3'-pyrrolidine]-5'S-yl-carboxylate;

decyl 1-[N-[1S-[1,3-di(octadecanoyloxy)-2-propyloxycarbonyl]-3-phenylpropyl]-S-alanyl]-3'S-spiro[(bicyclo[2.2.2]octane)-2,3'-pyrrolidine]-5'S-yl-carboxylate;

5-nonyl 1-[N-[1S-(1,3-dihydroxy-2-propyloxycarbonyl)-3-phenylpropyl]-S-alanyl]-3'S-spiro[(bicyclo[2.2.2]octane)-2,3'-pyrrolidine]-5'S-yl-carboxylate;

1,3-di-(hexadecanoyloxy)-2-propyl 2-[N-(1S-ethoxycarbonyl-3-phenylpropyl]-S-alanyl]-(1S,3S,5S)-2-azabicyclo[3.3.0]-7-octene-3-carboxylate;

(1-hexadecanoyloxy)-3-tetradecanoyloxy-2-propyl 2-[N-(1S-carboxy-3-phenylpropyl]-S-alanyl]-(1S,3S,5S)-2-azabicyclo[3.3.0]-7-octene-3-carboxylate;

1,3-di(9Z-octadecanoyloxy)-2-propyl 2-[N-(1S-nonyloxycarbonyl-3-phenylpropyl]-S-alanyl]-(1S,3S,5S)-2-azabicyclo[3.3.0]-7-octene-3-carboxylate;

1,3-di-(hexadecanoyloxy)-2-propyl 2-[N-(1S-[1,3-di(hexadecanoyloxy]-2-propyloxycarbonyl]-3-phenylpropyl]-S-alanyl]-(1S,3S,5S)-2-azabicyclo[3.3.0]-7-octene-3-carboxylate;

2-[N-[1S-(1,3-dihydroxy-2-propyloxycarbonyl)-3-phenylpropyl]-S-alanyl]-(1S,3S,5S)-2-azabicyclo[3.3.0]-7-octene-3-carboxylic acid;

benzhydryl 2-[N-[1S-[1,3-di(octadecanoyloxy)-2-propyloxycarbonyl]-3-phenylpropyl]-S-alanyl]-(1S,3S,5S)-2-azabicyclo[3.3.0]-7-octene-3-carboxylate;

1,3-di(hexadecanoyloxy)-2-propyl 1-[N-(1S-ethoxycarbonyl-3-phenylpropyl]-S-alanyl]-pyrrolidine-2S-carboxylate;

1,3-di(5Z,8Z,11Z,14Z-eicosatetraenoyloxy)-2-propyl 1-[N-(1S-carboxy-3-phenylpropyl-S-alanyl]-pyrrolidine-2S-carboxylate;

1,3-dihydroxy-2-propyl 1-[N-(1S-octyloxycarbonyl-3-phenylpropyl)-S-lysyl]-pyrrolidine-2S-carboxylate;

1,3-di(eicosanoyloxy)-2-propyl 1-[N-[1S-[1,3-di(eicosanoyloxy)-2-propyloxycarbonyl]-3-phenylpropyl]-S-alanyl]-pyrrolidine-2S-carboxylate;

5-nonyl 1-[N-[1S-[1,3-di(tetradecanoyloxy)-2-propyloxycarbonyl]-3-phenylpropyl]-S-lysyl]-pyrrolidine-2S-carboxylate; and undecyl 1-[N-[1S-[1,3-di(hexadecanoyloxy-2-propyloxycarbonyl]-3-phenylpropyl]-S-lysyl]-pyrrolidine-2S-carboxylate.

Possible salts of the compounds of the formula I are, according to the acid or basic nature of these compounds, alkali metal or alkaline earth metal salts or salts with physiologically tolerated amines or salts with inorganic or organic acids, such as, for example, HCl, HBr, $H_2SO_4$, maleic acid, fumaric acid, tartaric acid or citric acid.

The invention furthermore relates to a process for the preparation of compounds of the formula I, which comprises a) reacting a compound of the formula II $$R-(CH_2)_n-\underset{\underset{COOR^2}{|}}{CH}-NH-\underset{\underset{R^1}{|}}{CH}-\underset{\underset{O}{\|}}{C}-\underset{\underset{R^5}{|}}{N}-\underset{\underset{R^4}{|}}{CH}-COOH \quad (II)$$

in which R, $R^1$, $R^2$, $R^4$, $R^5$ and n have the same meaning as in formula I, with a compound of the formula IIIa/b $$HO-CH_2-\underset{\underset{OR^7}{|}}{CH}-CH_2-OR^8 \quad (IIIa)$$

$$\underset{\underset{CH_2-OR^8}{|}}{\underset{HO-CH}{|}}CH_2-OR^7 \quad (IIIb)$$

in which $R^7$ and $R^8$ have the same meaning as in formula I, using esterification methods with which the expert is familiar (see, for example, Buchler, Pearson, Survey of Organic Synthesis, Volume 1, New York 1970, pages 802-825; Houben-Weyl, Methoden der Organischen Chemie (Methods of Organic Chemistry), Volume E5, 1985, pages 656-773), for example under acid catalysis or after activation of the carboxylic acid function of II or of the hydroxyl function of IIIa/b, in particular under the conditions of a Mitsunobu reaction, in a suitable solvent at a temperature up to the boiling point of the reaction mixture,
or b) reacting a compound of the formula II in which R, $R^1$, $R^2$, $R^4$, $R^5$ and n have the same meaning as in formula I with a compound of the formula IVa/b

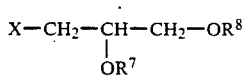

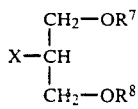

in which $R^7$ and $R^8$ have the same meaning as in formula I and in which X denotes a leaving group which can be displaced nucleophilically, in particular a Cl, Br or I atom or a sulfonic acid radical, under conditions of nucleophilic substitution, preferably in a polar organic solvent, such as an alcohol, preferably methanol, ethanol, propanol or isopropanol, or a lower ketone, preferably acetone, methyl ethyl ketone or methyl isobutyl ketone, or in acetonitrile, dimethylformamide, dimethyl sulfoxide or sulfolane or a hydrocarbon, preferably toluene, with or without the presence of an auxiliary base for trapping the acid formed, preferably in the presence of potassium bicarbonate, potassium carbonate, sodium bicarbonate, sodium carbonate, triethylamine, pyridine, 1,5-diazabicyclo[5,4,0]undec-5-ene or 1,5-diazabicyclo[4,3,0]-non-5-ene, and in the presence or absence of an alkali metal halide, preferably sodium iodide or potassium iodide, at a temperature between −50° C. and +100° C., preferably between −20° C. and +60° C., or c) reacting a compound of the formula V

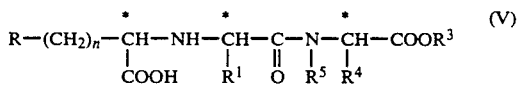

in which R, $R^1$, $R^3$, $R^4$, $R^5$ and n have the same meaning as in formula I, with a compound of the formula IIIa/b, as described under process variant a), or d) reacting a compound of the formula V in which R, $R^1$, $R^3$, $R^4$, $R^5$ and n have the same meaning as in formula I, with a compound of the formula IVa/b, as described under process variant b), or e) reacting a compound of the formula VI

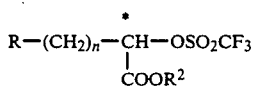

in which R, $R^2$ and n have the same meaning as in formula I, with a compound of the formula VII

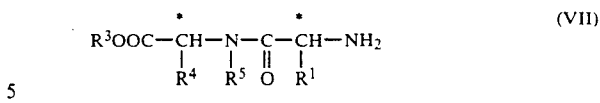

in which $R^1$, $R^3$, $R^4$ and $R^5$ have the same meaning as in formula I, for example by a procedure analogous to that described in U.S. Pat. No. 4,525,301, in a suitable solvent at a temperature up to the boiling point of the reaction mixture, or f) reacting a compound of the formula VII with a compound of the formula VIII

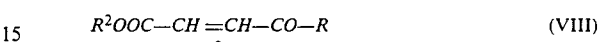

in which R and $R^2$ have the same meaning as in formula I, in a Michael reaction (Organikum, 6th edition, page 492, 1967) in a known manner, and hydrogenating the carbonyl group, for example in acid alcoholic solution, with a noble metal catalyst, in particular palladium or platinum on active charcoal, under a pressure of 20 to 120 bar, or g) reacting a compound of the formula VII with a compound of the formula IX

in which R, $R^2$ and n have the same meaning as in formula I, for example in accordance with the procedure described in J. Amer. Chem. Soc. 93, 2897 (1971), in a suitable solvent at a temperature up to the boiling point of the reaction mixture and reducing the resulting Schiff's bases, preferably using a complex hydride, for example sodium cyanoborohydride, or h) converting a compound of the formula X

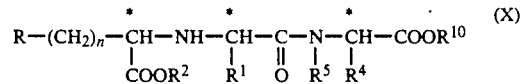

in which R, $R^1$, $R^2$, $R^4$, $R^5$ and n have the same meaning as in formula 1 and in which $R^{10}$ denotes a radical of the formula

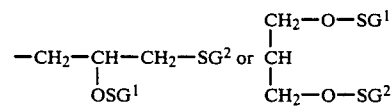

in which $SG^1$ and $SG^2$ are identical or different or denote a common easily removable protective group of a hydroxyl function, into a compound of the formula I in which $R^7$ and/or $R^8$ denote hydrogen by splitting off one or both protective groups by customary processes in a suitable solvent at a temperature up to the boiling point of the reaction mixture and if appropriate reacting this compound by acylation to give the end products of the formula I, or i) reacting a compound of the formula XI

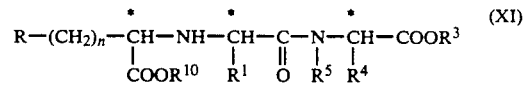

in which R, $R^1$, $R^2$, $R^4$, $R^5$ and n have the same meaning as in formula I and $R^{10}$ has the same meaning as in formula X, as described under process variant h) to give end products of the formula I, and if appropriate converting the compounds of the formula I thus obtained into their physiologically tolerated salts.

Compounds of the formulae II and V are known (see, for example, EP-A-79,022, EP-A-105,102, EP-A-113,880, EP-A-116,270, EP-A-74,164 and EP-A90,362).

Compounds of the formula III are known, for example from J. Org. Chem. 35, 2082 (1970), or they are prepared by an analogous route from the corresponding starting materials.

Compounds of the formula IV can be prepared, for example, from the compounds of the formula III by conversion of the hydroxyl function into a leaving group by customary processes.

Compounds of the formula VI in which $R^2$ denotes the radical

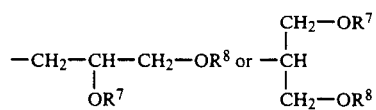

are obtained from compounds of the formula XII

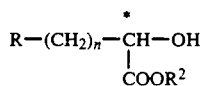
(XII)

in which R, $R^2$ and n have the same meaning as in formula I, by conversion of the hydroxyl function into the $-OSO_2CF_3$ group by customary processes.

Compounds of the formula VII are dipeptides which can be synthesized from the individual amino acid components by methods which are known per se in peptide chemistry (see, for example, Houben-Weyl, Methoden der Organischen Chemie (Methods of Organic Chemistry), Volume XV, Part II, pages 1 1-364).

Compounds of the formula VIII in which $R^2$ denotes the radical

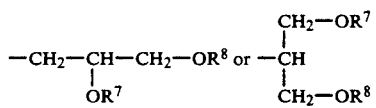

are obtained from compounds of the formula XIII $$HOOC-CH=CH-CO-R \qquad (XIII)$$

in which R has the same meaning as in formula I, by reaction with compounds of the formula IIIa/b under esterification conditions as described under process variant a), or by reaction with compounds of the formula IVa/b under the conditions of nucleophilic substitution, as described under process variant b).

Compounds of the formula IX in which $R^2$ denotes the radical

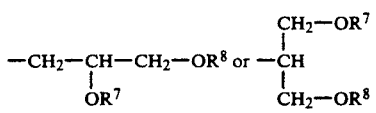

are obtained from compounds of the formula XIV

(XIV)

in which R and n have the same meaning as in formula I, by reaction with compounds of the formula IIIa/b under esterification conditions as described under process variant a), or by reaction with compounds of the formula IVa/b under the conditions of nucleophilic substitution as described under process variant b).

Compounds of the formula X can be prepared from compounds of the formula II by reaction with 1,2- or 1,3-protected glycerol derivatives, many of which are known, under esterification conditions such as are described under process variant a), or under conditions of nucleophilic substitution, such as are described under process variant b). Compounds of the formula XI are obtained from compounds of the formula III by an analogous route.

Compounds of the formula XII are obtained, for example, from compounds of the formula XV

(XV)

by alkylating esterifcation of the carboxyl group, subsequent protection of the hydroxyl function, for example with a protective group which can be removed hydrogenolytically, hydrolysis of the ester, subsequent reaction with a compound of the formula IIIa/b under esterification conditions, such as are described under process variant a), or with a compound of the formula IVa/b under the conditions of nucleophilic substitution, such as are described under process variant b), followed by removal of the hydroxyl-protective group, or by an equivalent reaction sequence.

Compounds of the formula XIII, XIV and XV are known.

The compounds of the formula I are glycerol esters of inhibitors of angiotensin-converting enzymes (ACE inhibitors). Triglycerides, especially those of medium- and long-chain fatty acids, have a specific absorption mechanism: after micellar intake into the enterocytes of the small intestine, they are discharged as constituents of chylomicrons not into venous blood but into the lymph. From there they pass into the blood, circumventing the liver (see, for example: L. Naupert et al., Klin. Wochenschrift 48, 449 (1970)).

The compounds of the formula I have different pharmacokinetics and a different tissue distribution to known ACE inhibitors, and in some representatives these properties manifest themselves in an increase in the central and a decrease in the peripheral effect. Under physiological conditions, they are split at least in part into the ACE inhibitors.

The compounds of the formula I and salts thereof have a long-lasting intense antihypertensive action. They can be used for combating high blood pressure of various origins. They can also be combined with other antihypertensive, vasodilating or diuretic compounds. Typical representatives of these classes of action are described, for example, in Erhardt-Ruschig, Arzneimittel (Medicaments), 2nd Edition, Weinheim, 1972. They can be used intravenously, subcutaneously or perorally.

The dosage for oral administration is 1-1,000 mg, preferably 1-400 mg, per individual dose for an adult patient of normal weight: this corresponds to about 15-13,000 μg/kg/day, preferably 15-5,000 μg/kg/day. In serious cases, it can also be increased, since no toxic properties have as yet been observed. It is also possible to reduce the dose, and is appropriate in particular if diuretics are administered at the same time.

On the basis of their pharmacological properties, the compounds of the formula I according to the invention are also suitable for treatment of cognitive dysfunctions of various origins, such as occur, for example, with Alzheimer's disease or senile dementia, in addition to combating blood pressure. The nootropic action of the compounds according to the invention has been tested on mice with a body weight of 20-25 g in the inhibitory (passive) avoidance test (step-through model). A modified form of the test method described by J. KOPP, Z. BODANECKY and M. E. JARVIK has been described by J. BURES, O. BURESOVA and J. HUSTON in "Techniques and Basic Experiments for the Study of Brain and Behavior", Elsevier Scientific Publishers, Amsterdam (1983).

According to this literature information, a substance is described as nootropic if it is capable of eliminating, in experimental animals, amnesia generated by means of an electroconvulsive shock or amnesia induced by means of scopolamine.

The experiments were carried out by modified test methods. The known nootropic agent 2-oxo-1-pyrrolidinylacetamide (piracetam) was used as the comparison compound. The clear superiority of the compounds according to the invention over the comparison substance manifested itself by the fact that scopolamine-induced amnesia can be eliminated in the inhibitory avoidance test with an MED (minimum effective dose) of 0.03-30 mg/kg p.o. The comparison substance has a MED of about 500-1,000 mg/kg p.o.

The invention thus furthermore relates to the use of the compounds according to the invention in the treatment and prophylaxis of cognitive dysfunctions.

The invention furthermore relates to medicaments containing the compounds mentioned, processes for their preparation and the use of the compounds according to the invention in the preparation of medicaments used for the treatment and prophylaxis of the above-mentioned diseases.

In carrying out the method according to the invention, the compounds of the formula I described above can be used on mammals, such as monkeys, dogs, cats, rats, humans and the like.

The medicaments are prepared by processes which are known per se and with which the expert is familiar. As medicaments, the pharmacologically active compounds according to the invention (=active compound) are used either as such or preferably in combination with suitable pharmaceutical auxiliaries in the form of tablets, coated tablets, capsules, suppositories, emulsions, suspensions or solutions, the active compound content being up to about 95%, advantageously between 10% and 75%.

The expert is familiar with the auxiliaries which are suitable for the desired medicament formulation the basis of his expert knowledge. In addition to solvents, gel-forming agents, suppository bases, tablet auxiliaries and other active compound excipients, it is also possible to use, for example, antioxidants, dispersing agents, emulsifiers, foam suppressants, flavor correctants, preservatives, solubilizing agents or dyestuffs.

The active compounds can be administered, for example, orally, rectally or parenterally (for example intravenously or subcutaneously), oral administration being preferred.

For an oral use form, the active compounds are mixed with the additives suitable for this purpose, such as excipients, stabilizers or inert diluents, and can be brought into suitable dosage forms, such as tablets, coated tablets, hard gelatin capsules, aqueous, alcoholic or oily suspensions or aqueous, alcoholic or oily solutions, by customary methods. Gum arabic, magnesia, magnesium carbonate, lactose, glucose or starch, in particular maize starch, for example, can be used as inert excipients. Formulation can be effected in the form of either dry or moist granules. Examples of possible oily excipients or solvents are vegetable or animal oils, such as sunflower oil or cod liver oil.

For subcutaneous or intravenous administration, the active compounds or physiologically tolerated salts thereof are dissolved, suspended or emulsified, if desired with the substances customary for this purpose, such as solubilizing agents, emulsifiers or other auxiliaries. Possible solvents are, for example, water, physiological saline solution or alcohols, for example ethanol, propanol or glycerol, and in addition also sugar solutions, such as solutions of glucose or mannitol, or a mixture of the various solvents mentioned.

The following Examples are intended to illustrate the compounds and processes according to the invention without limiting the invention to the substances mentioned here as representatives.

EXAMPLE 1

(1,3-Di(hexadecanoyloxy)-2-propyl 2-[N-(1S-ethoxycarbonyl-3-phenylpropyl]-S-alanyl]-(1S,3S,5S)-2-azabicyclo[3.3.0]-octane-3-carboxylate 2.75 g (10.5 mmol) of triphenylphosphine and 3.98 g (7.0 mmol) of 1,3-di(hexadecanoyloxy)-2-propanol are dissolved in 140 ml of absolute tetrahydrofuran, and a solution of 1.83 g (10.5 mmol) of diethyl azodicarboxylate in 15 ml of absolute tetrahydrofuran is added dropwise at 0° C. A ter 15 minutes at 0° C., a solution of 2.92 g (7.0 mmol) of 2-[N-(1S-ethoxycarbonyl-3-phenylpropyl)-S-alanyl]-(1S,3S,5S)-2-azabicyclo[3.3.0]octane-3-carboxylic acid (Ramipril) in 35 ml of absolute tetrahydrofuran is added dropwise and the mixture is subsequently stirred at 0° C. for one hour and at room temperature overnight. The reaction mixture is concentrated, the crude product is dissolved in 200 ml of ether, the solution is extracted with 3×100 ml of 2 N sodium hydroxide solution and 1×100 ml of water, the extract is dried over magnesium sulfate and concentrated and the residue is freed from impurities by chromatography on 1,100 g of silica gel (mobile phase methylene chloride/ethyl acetate 9:1, 8:2). 6.11 g (90%) of colorless waxy product are obtained.

$[\alpha]^{25}_D = -8.2°$ (c =1, methanol).

The following compounds are prepared analogously to the instructions given in Example 1 using suitable starting materials.

EXAMPLE 2

1,3-Di(decanoyloxy)-2-propyl
2-[-1S-ethyoxycarbonyl-3-phenylpropyl]-S-alanyl]-
(1S,3S,5S)-2-azabicyclo[3.3.0]-octane-3-carboxylate;

$[\alpha]^{25}_D = -11.5°$ (c = 1, methanol)

EXAMPLE 3

1,3-Di(octadecanoyloxy)-2-propyl
2-[N-(1S-ethoxycarbonyl-3-phenylpropyl]-S-alanyl]-
(1S,3S,5S)-2-azabicyclo[3.3.0]-octane-3-carboxylate;

$[\alpha]^{25}_D = -6.8°$ (c = 1, methanol).

EXAMPLE 4

1,3-DipiVloyloxy-2-propyl
2-[N-(1S-ethoxycarbonyl-3-phenylpropyl)-S-alanyl]-
(1S,3S,5S)-2-azabicyclo[3.3.0]-octane-3-carboxylate $[\alpha]^{20}_D = -17.5°$ (c = 1.22, methanol).

EXAMPLE 5

1,3-Dihydroxy-2-propyl
2-[N-(1S-ethoxycarbonyl-3-phenylpropyl)-S-alanyl]-
(1S,3S,5S)-2-azabicyclo[3.3.0]-octane-3-carboxylate 0.48 g (0.98 mmol) of 2-phenyl-1,3-dioxan-5-yl 2-[N-(1S-ethoxycarbonyl-3-phenylpropyl)-S-alanyl]-(1S,3S,5S)-2-azabicyclo[3.3.0]-octane-3-carboxylate and 1.5 g of p-toluenesulfonic acid are refluxed for 2 hours in 50 ml of tetrahydrofuran. The reaction solution is concentrated, the residue is taken up in ethyl acetate, the solution is washed several times with saturated sodium bicarbonate solution, dried and concentrated, and the residue is purified by column chromatography on silica gel (mobile phase toluene/ethanol 98:2, 95:5, 9:1). 0.056 g of the product is obtained. MS (FAB): 491 (M+1).

The 2-phenyl-1,3-dioxan-5-yl 2-[N-(1S-ethoxycarboynl-3-phenylpropyl)-S-alanyl]-(1S,3S,5S)-2-azabicyclo[3.3.0]-octane-3-carboxylate used as starting material is obtained analogously to Example 1 from 5-hydroxy-2-phenyl-1,3-dioxane and 2-[N-(1S-ethoxycarbonyl-3-phenylpropyl)-S-alanyl]-(1S,3S,5S)-2-azabicyclo[3.3.0]-octane-3-carboxylic acid (ramipril).

The following compounds can be prepared analogously to the instructions given in Example 1 using suitable starting materials.

1,3-di(hexadecanoyloxy)-2-propyl 2-[N-1S-ethoxycarbonyl3-phenylpropyl)-S-alanyl]-1,2,3,4-tetrahydroisoquinoline3S-carboxylate;

1,3-di-(9Z.12Z-octadecadienoyl)-2-propyl 2-[N-(1S-ethoxycarbonyl-3-phenylpropyl)-S-alanyl]-1,2,3,4-tetrahydroisoquinoline-3S-carboxylate;

1,3-di(tetradecanoyloxy)-2-propyl 2-[N-(1S-carboxy-3-phenylpropyl)-S-alanyl]-1,2,3,4-tetrahydroisoquinoline-3S-carboxylate;

2-[N-[1S-[1,3-di-(octadecanoyloxy)-2-propyloxycarbonyl]3-phenylpropyl)-S-alanyl]-1,2,3,4-tetrahydroisoquinoline-3S-carboxylic acid;

n-octyl 2-[N-[1S-[1,3-di-(9Z,12Z,15Z-octadecatrienoyloxy)-2-propyloxycarbonyl]-3-phenylpropyl]-S-alanyl]-1,2,3,4-tetrahydroisoquinoline-3S-carboxylate;

1,3-di(octadecanoyloxy)-2-propyl 1-[N-(1S-ethoxycarbonyl-3-phenylpropyl)-S-alanyl]-(2S,3aR,7aS)-octahydro[1H]indole-2-carboxylate;

1,3-di(5Z,8Z,11Z,14Z-eicosatetraenoyloxy)-2-propyl 1-[N-(1S-octyloxycarbonyl-3-phenylpropyl)-S-alanyl]-(2S,3aR,7aS)-octahydro[1H]indole-2-carboxylate;

1,3-di(hexadecanoyloxy)-2-propyl 1-[N-(1S-menthyloxycarbonyl-3-phenylpropyl)-S-alanyl]-(2S,3aR,7aS)-octahydro[1H]indole-2-carboxylate;

1,3-di(tetradecanoyloxy)-2-propyl 1-[N-(1S-[1,3-di(tetradecanoyloxy)-2-propyloxycarbonyl]-3-phenylpropyl)-S-alanyl]-(2S,3aR,7aS)-octahydro[1H]indole-2-carboxylate;

1,3-di(hexadecanoyloxy)-2-propyl 1-[N-(1S-carboxy-3-phenylpropyl)-S-alanyl]-(2S,3aS,7aS)-octahydro[1H]indole-2-carboxylate;

1,3-di(9Z,12Z,14Z-octadecatrienoyloxy)-2-propyl 1-[N-(1S-ethoxycarbonyl-3-phenylpropyl)-S-alanyl]-(2S,3aS,7aS)-octahydro[1H]indole-2-carboxylate;

1,3-di(hexadecanoyloxy)-2-propyl 1-[N-[1S-[1,3-di(hexadecanoyloxy)-2-propyloxycarbonyl]-3-phenylpropyl]-S-alanyl]-(2S,3aS,7aS)-octahydro[1H]indole-2-carboxylate;

1-[N-[1S-[1,3-di(octadecanoyloxy)-2-propyloxycarbonyl]3-phenylpropyl]-S-alanyl]-(2S,3aS,7aS)-octahydro[1H]indole-2-carboxylic acid;

benzhydryl 1-[N-[1S-[1,3-di(9Z-octadecanoyloxy)-2-propyloxycarbonyl]-3-phenylpropyl]-S-alanyl]-(2S,3aS,7aS)octahydro-[1H]indole-2-carboxylate;

1,3-di(5Z,8Z,11Z,14Z-eicosatetraenoyloxy)-2-propyl 2-[N-(1S-carboxy-3-phenylpropyl)-S-alanyl]-(1S,3S,5S)-2-azabicyclo[3.3.0]octane-3-carboxylate;

octyl 2-[N-[1S-[1,3-di(hexadecanoyloxy)-2-propyloxycarbonyl]-3-phenylpropyl]-S-alanyl]-(1S,3S,5S)-2-azabicyclo[3.3.0]octane-3-carboxylate;

2-[N-[1S-[1,3-di(octadecanoyloxy)-2-propyloxycarbonyl]3-phenylpropyl]-S-alanyl]-(1S,3S,5S)-2-azabicyclo[3.3.0]octane-3-carboxylic acid;

decyl 2-[N-[1S-[1,3-di(9Z,12Z-octadecadienoyloxy-2-propyloxycarbonyl]-3-phenylpropyl]-S-alanyl]-(1S,3S,5S)-2-azabicyclo[3.3.0]-octane-3-carboxylate;

1,3-dihexadecanoyloxy-2-propyl 1-[N-(1S-ethoxycarbonyl-3-phenylpropyl]-S-alanyl]-3'S-spiro[bicyclo[2.2.2]octane)-2,3'-pyrrolidine]-5'S-ylcarboxylate;

1-octadecanoyloxy-3-octadecanoyloxy-2-propyl 1-[N-(1S-octyloxycarbonyl-3-phenylpropyl)-S-alanyl]-3'S-spiro[(bicyclo[2.2.2]octane)-2,3'-pyrrolidine]-5'S-ylcarboxylate;

1,3-di(9Z,12Z,15Z-octadecatrienoyloxy)-2-propyl 1-[N-(1S-carboxy-3-phenylpropyl)-S-alanyl]-3'S-spiro[2.2.2]octane)-2,3'-pyrrolidine]-5'S-ylcarboxylate;

1,3-di(tetradecanoyloxy)-2-propyl 1-[N-[1S-[1,3-di(tetradecanoyloxy)-2-propyloxycarbonyl]-3-phenylpropyl]-S-alanyl]-3'S-spiro[(bicyclo[2.2.2]octane)-2,3'-pyrrolidine]-5'S-ylcarboxylate;

1,3-di(tetradacanoyloxy)-2-propyl 1-[N-[1S-[1,3-di(tetradecanoyloxy)-2-propyloxycarabonyl]-3-phenylpropyl]-S-alanyl]-3'S-spiro[(bicyclo[2.2.2]octane)-2,3'-pyrrolidine]5'S-ylcarboxylate;

decyl 1-[N-[1S-[1,3-di(octadecanoyloxy)-2-propyloxycarbonyl]-3-phenylpropyl]-S-alanyl]-3'S-spiro[(bicyclo[2.2.2]octane)-2,3'-pyrrolidine]-5'S-ylcarboxylate;

1,3-di(hexadecanoyloxy)-2-propyl 2-[N-(1S-ethoxycarbonyl3-phenylpropyl)-S-alanyl]-(1S,3S,5S)-2-azabicyclo[3.3.0]7-octene-3-carboxylate;

1-hexadecanoyloxy-3-tetradecanoyloxy-2-propyl 2-[N-(1S-carboxy-3-phenylpropyl)-S-alanyl]-(1S,3S,5S)-2-azabicyclo[3.3.0]-7-octene-3-carboxylate;

1,3-di(9Z-octadecanoyloxy)-2-propyl 2-[N-(1S-nonyloxycarbonyl-3-phenylpropyl)-S-alanyl]-

(1S,3S,5S)-2-azabicyclo[3.3.0]-7-octene-3-carboxylate;

1,3-di-(hexadecanoyloxy)-2-propyl 2-[N-(1S-[1,3-di(-hexadecanoyloxy]-2-propyloxycarbonyl]-3-phenylpropyl]-S-alanyl]-(1S,3S,5S)-2-azabicyclo[3.3.0]-7-octene-3-carboxylate;

benzhydryl 2-[N-[1S-[1,3-di(octadecanoyloxy)-2-propyloxycarbonyl]-3-phenylpropyl]-S-alanyl]-(1S,3S,5S)-2-azabicyclo[3.3.0]-7-octene-3-carboxylate;

1,3-di(hexadecanoyloxy)-2-propyl 1-[N-(1S-ethoxycarbonyl3-phenylpropyl)-S-alanyl]-pyrrolidine-2S-carboxylate;

1,3-di(5Z,8Z,11Z,14Z-eicosatetraenoyloxy)-2-propyl 1-[N-(1S-carboxy-3-phenylpropyl-S-alanyl]-pyrrolidine-2S-carboxylate;

1,3-di(eicosanoyloxy)-2-propyl 1-[N-[1S-[1,3-di(eicosanoyloxy)-2-propyloxycarbonyl]-3-phenylpropyl-S-alanyl]-pyrrolidine-2S-carboxylate;

5-nonyl 1-[N-[1S-[1,3-di(tetradecanoyloxy)-2-propyloxycarbonyl]-3-phenylpropyl-S-lysyl]-pyrrolidine-2S-carboxylate; and undecyl 1-[N-[1S-[1,3-di(hexadecanoyloxy-2-propyloxycarbonyl]-3-phenylpropyl-S-lysyl]-pyrrolidine-2S-carboxylate.

We claim:

1. A compound of the formula I

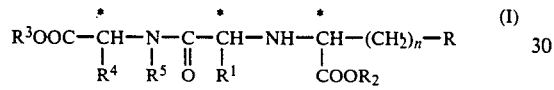

in which n = 1 or 2,

R = hydrogen, an unsubstituted or substituted aliphatic radical with 1-21 carbon atoms, wherein said aliphatic radical is an aliphatic acyclic radical having an open, straight or branched, saturated or unsaturated carbon chain, which, when substituted, is monosubstituted by amino, alkanoylamino, alkoxycarbonylamino, aroyloxycarbonylamino, arylalkoxycarbonylamino, arylakylamino, alkylamino, dialkylamino, alkylthio, aryloxy, arylthio, carboxy, carbamoyl, alkoxycarbonyl, alkanoyloxy, alkoxycarbonyloxy, aroyloxy, aryloxcarbonyloxy, aroylamino, guanidino, or aroyl, any of which may be further substituted in the aryl part as defined below for said aromatic radicals, or, wherein said radical is carboxy or carbamoyl, an unsubstituted or substituted alicyclic radical with 3-20 carbon atoms, wherein said alicyclic radical is an isocyclic non-aromatic radical which may carry one or more open-chain aliphatic side-chains, which radical may contain one or more fused, spiro-linked or isolated rings, and which radical, when substituted, is mono-, di-, or trisubstituted by $(C_1-C_8)$-alkyl, $(C_1-C_4)$-alkoxy, hydroxyl, halogen, nitro, amino, aminomethyl, $(C_1-C_4)$-alkylamino, di-$(C_1-C_4)$-alkylamino, $(C_1-C_4)$-alkanoylamino, methylenedioxy, carboxyl, cyano and/or sulfamoyl, an unsubstituted or substituted aromatic radical with 6-12 c carbon atoms, which, when substituted, is mono-, di- or trisubstituted by $(C_1-C_8)$-alkyl, $(C_1-C_4)$-alkoxy hydroxy, halogen, nitro, amino, aminomethyl, $(C_1-C_4)$-alkylamino, di-$(C_1-C_4)$-alkylamino, $(C_1-C_4)$-alkanoylamino, methylenedioxy, carboxyl, cyano and/or sulfamoyl, an unsubstituted or substituted araliphatic radical with 7-32 carbon atoms, wherein said araliphatic radical is an aromatic-aliphatic radical in which said aromatic and aliphatic parts are unsubstituted or substituted as defined above, or wherein said radical is phthalidyl, indanyl or fluorenyl, any of which may be unsubstituted or substituted as defined above for said aromatic radicals, an unsubstituted or substituted alicyclic-aliphatic radical with 7-14 carbon atoms, wherein said aliphatic and alicyclic parts are unsubstituted or substituted as defined above, an unsubstituted or substituted heteroaromatic or heteroaromatic-$(C_1-C_8)$-aliphatic radial, wherein said aliphatic radical, when present, is unsubstituted or substituted as defined above and said heteroaromatic radical is a ring system which is thienyl, benzo[b]thienyl, furyl, benzofuryl, pyrrolyl, isoindolyl or indolyl, which ring system may be unhydrogenated, partly, or completely hydrogenated, and which, when substituted on the heteroaromatic part, is substituted as above for said aromatic radicals, or a racial $OR^a$ or $SR^a$, in which $R^a$ denotes an unsubstituted or substituted aliphatic radical, defined as above, with 1-4 carbon atoms, or an unsubstituted or substituted aromatic radical, defined as above, with 6-12 carbon atoms or an unsubstituted or substituted heteroaromatic radical, defined as above, or an arylalkyl radical which may be substituted in the aryl part as defined above for said aromatic radicals;

$R^1$ denotes hydrogen, an unsubstituted or substituted aliphatic radical, defined as above, with 1-21 carbon atoms, an unsubstituted or substituted alicyclic radical, defined as above, with 3-20 carbon atoms, an unsubstituted or substituted alicyclic-aliphatic radical, defined as above, with 4-20 carbon atoms, an unsubstituted or substituted aromatic radical, defined as above, with 6-12 carbon atoms, an unsubstituted or substituted araliphatic radical, defined as above, with 7-32 carbon atoms, an unsubstituted or substituted heteroaromatic or heteroaromatic-$(C_1-C_8)$-aliphatic radical, defined as above, or, if not already included in the above definitions, the side chain, which may be protected or unprotected, of a naturally occurring α-amino acid;

$R^2$ and $R^3$ are identical or different and denote hydrogen, an unsubstituted or substituted aliphatic radical, defined as above, with 1-21 carbon atoms, an unsubstituted or substituted alicyclic radical, defined as above, with 3-20 carbon atoms, an unsubstituted or substituted aromatic radical, defined as above, with 6-12 carbon atoms, an unsubstituted or substituted araliphatic radical, defined as above, with 7-32 carbon atoms, a radical of the formula

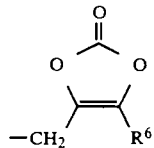

in which $R^6$ is hydrogen, an aliphatic radical, defined as above, with 1-6 carbon atoms or an unsubstituted or substituted aromatic radical, defined as above, with 6-12 carbon atoms, a radical of the formula

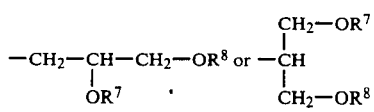

in which $R^7$ and $R^8$ are identical or different and independently of one another denote hydrogen, an unsubstituted or substituted, unbranched or branched, saturated or unsaturated, alkyl radical with 1-23 carbon atoms, which, when substituted, is substituted as defined above for said aliphatic radicals, or an unbranched or branched, saturated or unsaturated, acyl radical with 1-23 carbon atoms, where said acyl radical may be unsubstituted or substituted by keto, hydroxyl or, if not already included in the above definitions, those substituents which maybe present on natural triglycerides, in which at least one of the radicals $R^2$ or $R^3$ denotes a radical of the formula

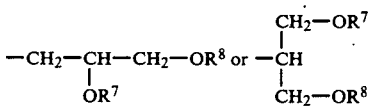

and $R^4$ and $R^5$, together with the atoms carrying them, form a ring system which is an octahydroindole; octahydrocyclopenta[b]pyrrole; decahydrocyclohepta[b]pyrrole; hexahydrocyclopropa[b]pyrrole; octahydroisoindole; octahydrocyclopenta[c]pyrrole; 2,3,3a,4,5,7a-hexahydroindole; 1,2,3,3a,4,6a-hexahyrocyclopenta[b]pyrrole; pyrrolidine or indoline ring system; wherein said ring system is unsubstituted or monosubstituted by $(C_6-C_{12})$-aryl, $(C_6-C_{12})$-hydroxyaryl, $(C_6-C_{12})$-arylmercapto or $(C_3-C_7)$-cycloalkyl, and which may be, in the aryl portion of indoline, mono- or disubstituted by $(C_1-C_6)$-alkoxy;

or a physiologically tolerated salt thereof with an acid or base.

2. A compound of the formula I as claimed in claim 1, in which a) n = 1 or 2;

b) R 1. denotes hydrogen;
2. denotes alkyl with 1-18 carbon atoms;
3. denotes an aliphatic acyclic radical of the formula $C_aH_{(2a-b+1)}$, in which double bonds, if their number exceeds 1, are not cumulative, a stands for an integer from 2 to 18 and b stands for an integer from 2 to a;
4. denotes a mono-, di-, tri-, tetra- or pentacyclic, non-aromatic hydrocarbon radical of the formula $C_cH_{(2c-d-1)}$, which is optionally branched, in which c stands for an integer from 3 to 20 and d stands for an even number from 0 to (C-2);
5. denotes aryl which has 6-12 carbon atoms and can be mono-, di- or trisubstituted by $(C_1-C_8)$-alkyl, $(C_1-C_4)$alkoxy, hydroxyl, halogen, nitro, amino, aminomethyl, $(C_1-C_4)$alkylamino, di-$(C_1-C_4)$-alkylamino, $(C_1-C_4)$alkanoylamino, methylenedioxy, carboxyl, cyano and/or sulfamoyl;
6. if n = 2, denotes $(C_6-C_{12})$-aryl-$(C_1-C_8)$alkyl or di-$(C_6-C_{12})$-aryl-$(C_1-C_8)$-alkyl, each of which can be substituted in the aryl part as described under b) 5.; or denotes
7. alkoxy with 1-4 carbon atoms;
8. aryloxy which has 6-12 carbon atoms and can be substituted as described under b) 5.;
9. heteroaromatic or heteroaromatic $(C_1-C_8)$-alkyl which can be substituted in the heteroaromatic as described under b) 5.;
10. amino-$(C_1-C_8)$-alkyl;
11. $(C_1-C_4)$-alkanoylamino-$(C_1-C_8)$-alkyl;
12. $(C_7-C_{13})$-aroylamino-$(C_1-C_8)$-alkyl;
13. $(C_1-C_4)$-alkoxycarbonylamino-$(C_1-C_8)$-alkyl;
14. $(C_6-C_{12})$-aryl-$(C_1-C_4)$-alkoxycarbonylamino-$(C_1-C_8)$-alkyl;
15. $(C_6-C_{12})$-aryl-$(C_1-C_4)$-alkylamino-$(C_1-C_8)$-alkyl;
16. $(C_1-C_4)$-alkylamino-$(C_1-C_8)$-alkyl;
17. di-$(C_1-C_4)$-alkylamino-$(C_1-C_8)$-alkyl;
18. guanidino-$(C_1-C_8)$-alkyl;
19. imidazolyl;
20. indolyl;
21. $(C_1-C_4)$-alkylthio;
22. if n = 2, $(C_1-C_4)$-alkylthio-$(C_1-C_8)$-alkyl;
23. $(C_6-C_{12})$-arylthio-$(C_1-C_8)$-alkyl; which can be substituted in the aryl part as described under b) 5.;
24. $(C_6-C_{12})$-aryl-$(C_1-C_8)$-alkylthio, which can be substituted in the aryl part as described under b) 5.;
25. if n = 2, carboxy-$(C_1-C_8)$-alkyl;
26. carboxyl;
27. carbamoyl;
28. if n = 2, carbamoyl-$(C_1-C_8)$-alkyl;
29. $(C_1-C_4)$-alkoxycarbonyl-$(C_1-C_8)$-alkyl;
30. if n = 2, $(C_6-C_{12})$-aryloxy-$(C_1-C_8)$-alkyl, which can be substituted in the aryl part as described under b) 5.; or
31. $(C_6-C_{12})$-aryl-$(C_1-C_8)$-alkoxy, which can be substituted in the aryl part as described under b) 5.;

c) $R^1$ 1. denotes hydrogen;
2. denotes alkyl with 1-18 carbon atoms;
3. denotes an aliphatic acyclic radical of the formula $C_aH_{(2a-b+1)}$, wherein double bonds, if their number exceeds 1, are not cumulative, a stands for an integer from 2 to 18 and b stands for an even number from 2 to a;
4. denotes a mono-, di-, tri-, tetra- or pentacyclic, non-aromatic hydrocarbon radical of the formula $C_cH_{(2c-d-1)}$, which is optionally branched and in which c stands for an integer from 3 to 20 and d stands for an even number from 0 to (c-2); or denotes 5. aryl with 6-12 carbon atoms, which can be substituted as described under b) 5.;
6. $(C_6-C_{12})$-aryl-$(C_1-C_8)$-alkyl or $(C_7-C_{13})$-aroyl-$(C_1-C_8)$-alkyl, both of which can be substituted in the aryl part as described under b) 5.;
7. mono- or bicyclic optionally partly hydrogenated heteroaromatic or heteroaromatic-$(C_1-C_8)$-alkyl which can be substituted in the heteroaromatic as described for aryl under b) 5.; or
8. if not yet included in c) 1.-7., the side chain, protected if appropriate, of a naturally occurring α-amino acid of the formula $R^1$—CH(NH$_2$)—COOH;

d) $R^2$ and $R^3$ are identical or different and
1. denote hydrogen;
2. denote alkyl with 1-18 carbon atoms;
3. denote an aliphatic acyclic radical of the formula $C_aH_{(2a-b+1)}$, in which double bonds, if their number exceeds 1, are not cumulative, a stands for an integer from 2 to 18 and b stands for an even number from 2 to a;
4. denote a mono-, di-, tri-, tetra- or pentacyclic, non-aromatic hydrocarbon radical of the formula $C_cH_{(2c-d-1)}$, which is optionally branched and in which c stands for an integer from 3 to 20 and d stands for an even number from 0 to (c-2); or denote
5. di-$(C_1-C_4)$-alkylamino-$(C_1-C_8)$-alkyl;
6. $(C_1-C_5)$-alkanoyloxy-$(C_1-C_8)$-alkyl;
7. $(C_1-C_6)$-alkoxycarbonyloxy-$(C_1-C_8)$-alkyl;
8. $(C_7-C_{13})$-aroyloxy-$(C_1-C_8)$-alkyl;
9. $(C_6-C_{12})$-aryloxycarbonyloxy-$(C_1-C_8)$-alkyl;
10. aryl with 6-12 carbon atoms;
11. $(C_7-C_{20})$-aralkyl;
12. phthalidyl;
13. a radical of the formula

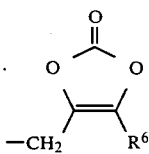

in which $R^6$ is hydrogen, $(C_1-C_6)$-alkyl or aryl with 6-12 carbon atoms, or
14. a radical of the formula

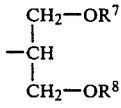

in which $R^7$ and $R^8$ are identical or different and independently of one another denote hydrogen, an optionally substituted unbranched or branched saturated or unsaturated alkyl radical with 1-23 carbon atoms or an optionally substituted unbranched or branched saturated or unsaturated acyl radical with 1-23 carbon atoms, it being possible for the radicals mentioned under d) 8., 9., 10., 11. and 12. to be substituted in the aryl part as described under b) 5.; and
in which at least one of the radicals $R^2$ or $R^3$ denotes a radical of the formula

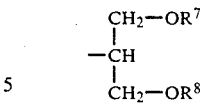

and physiologically tolerated salts thereof with acids and bases.

3. A compound of the formula I as claimed in claim 1 in which
n = 1 or 2,
R = hydrogen,
  alkyl with 1-8 carbon atoms,
  alkenyl with 2-6 carbon atoms,
  cycloalkyl with 3-9 carbon atoms,
  aryl which has 6-12 carbon atoms, and can be mono-, di- or trisubstituted by $(C_1-C_4)$-alkyl, $(C_1-C_4)$-alkoxy, hydroxyl, halogen, nitro, amino, aminomethyl $(C_1-C_4)$-alkylamino, di-$(C_1-C_4)$-alkylamino, $(C_1-C_4)$-alkanoylamino, methylenedioxy, carboxyl, cyano and/or sulfamoyl,
  alkoxy with 1-4 carbon atoms,
  aryloxy which has 6-12 carbon atoms and can be substituted as described above for aryl, mono- or bicyclic heteroaromatic which can be substituted as described above for aryl,
  amino-$(C_1-C_4)$-alkyl,
  $(C_1-C_4)$-alkanoylamino-$(C_1-C_4)$-alkyl,
  $(C_7-C_{13})$-aroylamino-$(C_1-C_4)$-alkyl,
  $(C_1-C_4)$-alkoxycarbonylamino-$(C_1-C_4)$-alkyl,
  $(C_6-C_{12})$-aryl-$(C_1-C_4)$-alkoxycarbonylamino-$(C_1-C_4)$alkyl,
  $(C_6-C_{12})$-aryl-$(C_1-C_4)$-alkylamino-$(C_1-C_4)$-alkyl,
  $(C_1-C_4)$-alkylamino-$(C_1-C_4)$-alkyl,
  di-$(C_1-C_4$-alkylamino-$(C_1-C_4)$-alkyl,
  35 guanidino-$(C_1-C_4)$-alkyl,
  imidazolyl, indolyl,
  $(C_1-C_4)$-alkylthio,
  $(C_1-C_4)$-alkylthio-$(C_1-C_4)$-alkyl,
  $(C_6-C_{12})$-arylthio-$(C_1-C_4)$-alkyl,
    which can be substituted in the aryl part as described above for aryl,
  $(C_6-C_{12})$-aryl-$(C_1-C_4)$-alkylthio,
    which can be substituted in the aryl part as described above for aryl,
  carboxy-$(C_1-C_4)$-alkyl,
  carboxyl, carbamoyl,
  carbamoyl-$(C_1-C_4)$-alkyl,
  $(C_1-C_4)$-alkoxycarbonyl-$(C_1-C_4)$-alkyl,
  $(C_6-C_{12})$-aryloxy-$(C_1-C_4)$-alkyl,
    which can be substituted in the aryl part as described above for aryl, or
  $(C_6-C_{12})$-aryl-$(C_1-C_4)$-alkoxy,
    which can be substituted in the aryl part as described above for aryl,
$R^1$ denotes hydrogen,
  alkyl with 1-6 carbon atoms,
  alkenyl with 2-6 carbon atoms,
  alkynyl with 2-6 carbon atoms,
  cycloalkyl with 3-9 carbon atoms,
  cycloalkenyl with 5-9 carbon atoms,
  $(C_3-C_9)$-cycloalkyl-$(C_1-C_4)$-alkyl,
  $(C_5-C_9)$-cycloalkenyl- $C_1-C_4)$-alkyl,
  optionally partly hydrogenated aryl which has 6-12 carbon atoms
  and can be substituted as described above for R,
  $(C_6-C_{12})$-aryl-$(C_1-C_4)$-alkyl or $(C_7-C_{13})$-aroyl(C ($C_1$ or $C_2$)-alkyl both of which can be substituted like the above aryl, which can be substituted like the above aryl, or the side chain, protected if appropriate, of a naturally occurring α-amino acid $R^1$—CH(NH$_2$)—COOH, and $R^3$ are identical or different and denote hydrogen, alkyl with 1-6 carbon atoms,
alkenyl with 2-6 carbon atoms,
di-($C_1$-$C_4$)-alkylamino-($C_1$-$C_4$)-alkyl,
($C_1$-$C_5$)-alkanoyloxy-($C_1$-$C_4$)-alkyl,
($C_1$-$C_6$)-alkoxycarbonyloxy-($C_1$-$C_4$)-alkyl,
($C_7$-$C_{13}$)-aroyloxy-($C_1$-$C_4$)-alkyl,
($C_6$-$C_{12}$)-aryloxycarbonyloxy-($C_1$-$C_4$)-alkyl,
aryl with 6-12 carbon atoms,
($C_6$-$C_{12}$)-aryl-($C_1$-$C_4$)-alkyl,
($C_3$-$C_9$)-cycloalkyl,
($C_3$-$C_9$)-cycloalkyl-($C_1$-$C_4$)-alkyl,
phthalidyl,
a radical of the formula

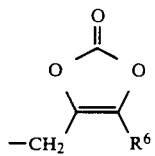

in which $R^6$ is hydrogen, ($C_1$-$C_6$)-alkyl or aryl with 6-12 carbon atoms,
or a radical of the formula

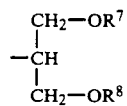

in which $R^7$ and $R^8$ are identical or different and independently of one another denote hydrogen or an optionally substituted unbranched or branched saturated or unsaturated acyl radical with 1-23 carbon atoms, and in which at least one of the radicals $R^2$ or $R^3$ denotes a radical of the formula

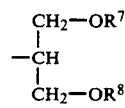

and $R^4$ and $R^5$ have the abovementioned meaning, and physiologically tolerated salts thereof with acids or base.

4. A compound of the formula I as claimed in claim 1, in which n = 1 or 2,

R denotes ($C_1$-$C_6$)-alkyl, ($C_2$-$C_6$)-alkenyl, ($C_3$-$C_9$)-cycloalkyl, amino-($C_1$-$C_4$)-alkyl, ($C_2$-$C_5$)-acylamino($C_1$-$C_4$)-alkyl, ($C_7$-$C_{13}$)-aroylamino-($C_1$-$C_4$)-alkyl, ($C_1$-$C_4$)-alkoxycabonylamino-($C_1$-$C_4$)-alkyl, ($C_6$-$C_{12}$)-aryl-($C_1$-$C_4$)-alkoxycarbonylamino-($C_1$-$C_4$)-alkyl, ($C_6$-$C_{12}$)-aryl, which can be mono-, di- or tri-substituted by ($C_1$-$C_4$)-alkyl, ($C_1$-$C_4$)-alkoxy, hydroxyl, halogen, nitro, amino, ($C_1$-$C_4$)-alkylamino, di-($C_1$-$C_4$)-alkylamino and/or methylenedioxy, or 3-indolyl, $R^1$ denotes hydrogen or ($C_1$-$C_6$)-alkyl, which is unsubstituted or substituted by amino, ($C_1$-$C_6$)-acylamino or benzoylamino, ($C_2$-$C_6$)-alkenyl, ($C_3$-$C_9$)-cycloalkyl, ($C_5$-$C_9$)-cycloalkenyl, ($C_3$-$C_7$)-cycloalkyl-($C_1$-$C_4$)-alkyl, ($C_6$-$C_{12}$)-aryl or partly hydrogenated aryl, each of which can be substituted by ($C_1$-$C_4$)-alkyl, ($C_1$ or $C_2$)-alkoxy or halogen, ($C_6$-$C_{12}$)-aryl-($C_1$-$C_4$)-alkyl or ($C_7$-$C_{13}$)-aroyl-($C_1$-$C_2$)-alkyl, both of which can be substituted in the aryl radical as defined above, a heteroaromatic or heteroaromatic ($C_1$-$C_8$)-alkyl, $R^2$ and $R^3$ are identical or different radicals and denote hydrogen, ($C_1$-$C_6$)-alkyl, ($C_2$-$C_6$)-alkenyl, ($C_6$-$C_{12}$)-aryl-($C_1$-$C_4$)-alkyl, ($C_1$-$C_5$)-alkanoyloxy-($C_1$-$C_4$)-alkyl, ($C_1$-$C_6$)-alkoxycarbonyloxy-($C_1$-$C_4$)-alkyl, ($C_7$-$C_{13}$)-aroyloxy-($C_1$-$C_4$)-alkyl, ($C_6$-$C_{12}$)-aryloxycarbonyloxy-($C_1$-$C_4$)-alkyl, phthalidyl, a radical of the formula

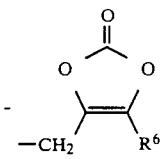

in which $R^6$ is hydrogen, ($C_1$-$C_6$)-alkyl or aryl with 6-12 carbon atoms, or a radical of the formula

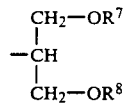

in which $R^7$ and $R^8$ denote hydrogen or a saturated or unsaturated acyl radical with 8-23 carbon atoms, and in which at least one of the radicals $R^2$ or $R^3$ denotes a radical of the formula

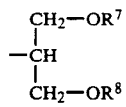

and $R^4$ and $R^5$ have the abovementioned meaning, and physiologically tolerated salts thereof with acids or base.

5. A compound of the formula I as claimed in claim 1, wherein $R^4$ and $R^5$, together with the atoms carrying them, form octahydroindole; octahydrocyclopenta[b]pyrrole; decahydrocyclohepta[b]pyrrole; hexahydrocyclopropa[b]pyrrole; octahydroisoindole; octahydrocyclopenta[c]pyrrole; 2,3,3a,4,5,7a-hexahydroindole; 1,2,3,3a,4,6a-hexahyrocyclopenta[b]pyrrole; pyrrolidine or indoline;

or a physiologically tolerated salt thereof with an acid or base.

6. A compound of the formula I as claimed in claim 1, in which n = 1 or 2,

R denotes methoyl, ethyl, cyclohexyl, tert.-butoxycarbonylamino($C_1$-$C_4$)-alkyl, benzoyloxycarbonylamino-($C_1$-$C_4$)-alkyl or phenyl, which can be mono- or disubstituted, or in the case of methoxy trisubstituted, by phenyl, $(C_1-C_2)$-alkyl, $(C_1$ or $C_2)$-alkoxy, hydroxyl, fluorine, chlorine, bromine, amino, $(C_1-C_4)$-alkylamino, di-$(C_1-C_4)$-alkylamino, nitro and/or methylenedioxy, $R^1$ denotes hydrogen, $(C_1-C_3)$-alkyl, $(C_2$ or $C_3)$-alkenyl, the side chain, protected if appropriate, of lysine, phenylalanine or tyrosine, benzyl, 4-methoxybenzyl, 4-ethoxybenzyl, phenethyl, 4-aminobutyl or benzoylmethyl, $R^2$ and $R^3$ are identical or different radicals and denote hydrogen, $(C_1-C_6)$-alkyl, $(C_2-C_6)$-alkenyl, $(C_6-C_{12})$-aryl-$(C_1-C_4)$-alkyl, $(C_1-C_5)$-alkanoyloxy-$(C_1-C_4)$-alkyl, $(C_1-C_6)$-alkoxycarbonyloxy-$(C_1-C_4)$-alkyl, $(C_7-C_{13})$-aroyloxy-$(C_1-C_4)$-alkyl, $(C_6-C_{12})$-aryloxycarbonyloxy-$(C_1-C_4)$-alkyl, phthalidyl, a radical of the formula

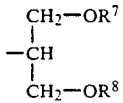

in which $R^6$ is hydrogen, $(C_1-C_6)$-alkyl or aryl with 6-12 carbon atoms, or a radical of the formula

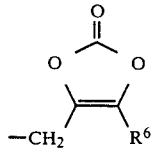

in which $R^7$ and $R^8$ denote hydrogen or a saturated or unsaturated acyl radical with 8-23 carbon atoms, and in which at least one of the radicals $R^2$ or $R^3$ denotes a radical of the formula

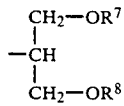

and $R^4$ and $R^5$ have the abovementioned meaning, or a physiologically tolerated salt thereof with an acid or base.

7. A compound as claimed in claim 1, which compound is 1,3-d(hexadecanoyloxy)-2-propyl 2-[N-(1S-ethoxycarbonyl-3-phenylpropyl)-S-alanyl]-(1S,3S,5S)-2-azabicyclo[3.3.0]octane-3-carboxylate, or a physiologically tolerated salt thereof with an acid or base.

8. A method of treating at least one cognitive dysfunction, comprising the step of administering to a mammal in recognized need of and for the purpose of said treatment an amount of a compound of formula I or a physiologically acceptable salt thereof as claimed in claim 1, effective for said treatment.

9. A pharmaceutical composition comprising a compound of formula I or a physiologically acceptable salt thereof as claimed in claim 1, and a physiologically acceptable carrier.

10. A pharmaceutical composition as claimed in claim 9, wherein said composition comprises an amount of said compound of formula I or physiologically acceptable salt thereof effective for the treatment of at least one cognitive dysfunction.

* * * * *

UNITED STATES PATENT AND TRADEMARK OFFICE
CERTIFICATE OF CORRECTION

PATENT NO. : 5,055,483
DATED : October 08, 1991
INVENTOR(S) : Wolfgang Ruger et al.

It is certified that error appears in the above-identified patent and that said Letters Patent is hereby corrected as shown below:

In the Abstract, lines 1-2, after "formula" insrt --I--.
Claim 1, column 23, line 43, "arylakylamino" should read --arylalkylamino--.
Claim 1, column 23, lines 46-47, "aryloxcarbonyloxy" should read --aryloxycarbonyloxy--.
Claim 1, column 23, line 65, after "6-12" delete "c".
Claim 1, column 23, line 67, "hydroxy" should read -- ,hydroxyl--.
Claim 1, column 24, line 18, "radial" should read --radical--.
Claim 1, column 24, line 29, "racial" should read --radical--.
Claim 1, column 25, line 31, "maybe" should read --may be--.
Claim 1, column 25, line 49, "hexahyrocyclopenta[b]pyrrole" should read --hexahydrocyclopenta[b]pyrrole.
Claim 2, column 26, line 5, "(C-2)" should read --(c-2)--.
Claim 2, column 28, line 7, before "physiologically" insert --e) $R^4$ and $R^5$, together with the atoms carrying them, are as defined above; or a-- ; "salts" should read --salt--; and "acids" should read --acid--.

UNITED STATES PATENT AND TRADEMARK OFFICE
CERTIFICATE OF CORRECTION

PATENT NO. : 5,055,483
DATED     : October 08, 1991
INVENTOR(S) : Wolfgang Ruger et al.

It is certified that error appears in the above-identified patent and that said Letters Patent is hereby corrected as shown below:

Claim 2, column 28, line 8, "and bases" should read --or base--.

Claim 3, column 28, line 19, after "aminomethyl" insert --,--.

Claim 3, column 28, line 35, "$C_4$-" should read to --$C_4$.

Claim 3, column 28, line 36, delete "35".

Claim 3, column 28, linje 68, "aroyl(C" should read --aroyl- --.

Claim 3, column 29, line 2, after "aryl," insert --heteroaromatic or heteroaromatic ($C_1$-$C_8$)-alkyl.

Claim 3, column 29, line 7, before "and $R^3$" insert $R_2$.

Claim 3, column 29, line 55, after "meaning," "and" should read --or a--.

Claim 3, column 29, line 56, "salts" should read --salt-- and "acids" should read --an acid--.

Claim 4, column 29, line 64, "alkoxycabonylamino" should read --alkoxycarbonylamino--.

Claim 4, column 30, line 13, after "alkyl," insert --or a side chain of a naturally occurring α-amino acid which is protected if appropiate--.

UNITED STATES PATENT AND TRADEMARK OFFICE
CERTIFICATE OF CORRECTION

PATENT NO. : 5,055,483
DATED : October 8, 1991
INVENTOR(S) : Wolfgang Ruger et al It is certified that error appears in the above-indentified patent and that said Letters Patent is hereby corrected as shown below:

Claim 4, column 30, line 50, after "meaning" "and" should read --or a --.

Claim 4, column 30, line 51, "salts" should be --salt-- and "acids" should read --an acid--.

Claim 5, column 30, line 55, after "form" insert --an unsubstituted ring system which is--.

Claim 5, column 30, line 59, "hexahyrocyclopenta[b]pyrrole" should read --hexahydrocyclopenta[b]pyrrole--.

Claim 6, column 30, line 66, "methoyl" should read --methyl--.

Claim 7, column 32, line 16, "-d(" should read "-di(--.

Signed and Sealed this

Twenty-fourth Day of August, 1993

Attest:

BRUCE LEHMAN

*Attesting Officer*  *Commissioner of Patents and Trademarks*